United States Patent [19]

Dieguez

[11] Patent Number: 4,991,449
[45] Date of Patent: Feb. 12, 1991

[54] METHOD AND APPARATUS FOR SAMPLING A CRYOGENIC LIQUID FOR ANALYSIS

[75] Inventor: José M. Dieguez, Saint-Bruno, Canada

[73] Assignee: Canadian Liquid Air Ltd-Air Liquide Canada LTEE, Montreal, Canada

[21] Appl. No.: 374,762

[22] Filed: Jul. 3, 1989

[51] Int. Cl.⁵ ............................................. G01N 1/00
[52] U.S. Cl. .................................................. 73/863.11
[58] Field of Search .............. 73/863.11, 863.12, 864, 73/864.51, 864.63, 864.91, 863.86, 863.81

[56] References Cited

U.S. PATENT DOCUMENTS

| | | | |
|---|---|---|---|
| 3,029,627 | 4/1962 | Buban | 73/19 |
| 3,123,982 | 3/1964 | Brown et al. | 73/863.11 |
| 3,357,256 | 12/1967 | Burch | 73/863.11 |
| 3,938,391 | 2/1976 | Winkler | 73/863.11 |

*Primary Examiner*—Robert Raevis
*Attorney, Agent, or Firm*—Oblon, Spivak, McClelland, Maier & Neustadt

[57] ABSTRACT

A method and apparatus for sampling a cryogenic liquid for determination of its molar composition involves isolating a sample of the liquid under conditions to avoid fractionation of the sample, especially isothermal conditions, removing the conditions, allowing the liquid to vaporize intact and collecting the vaporized liquid in gas form; in particular the vaporized liquid is collected in a collection vessel which may be detached from the balance of the system and transported to a site of analysis.

10 Claims, 1 Drawing Sheet

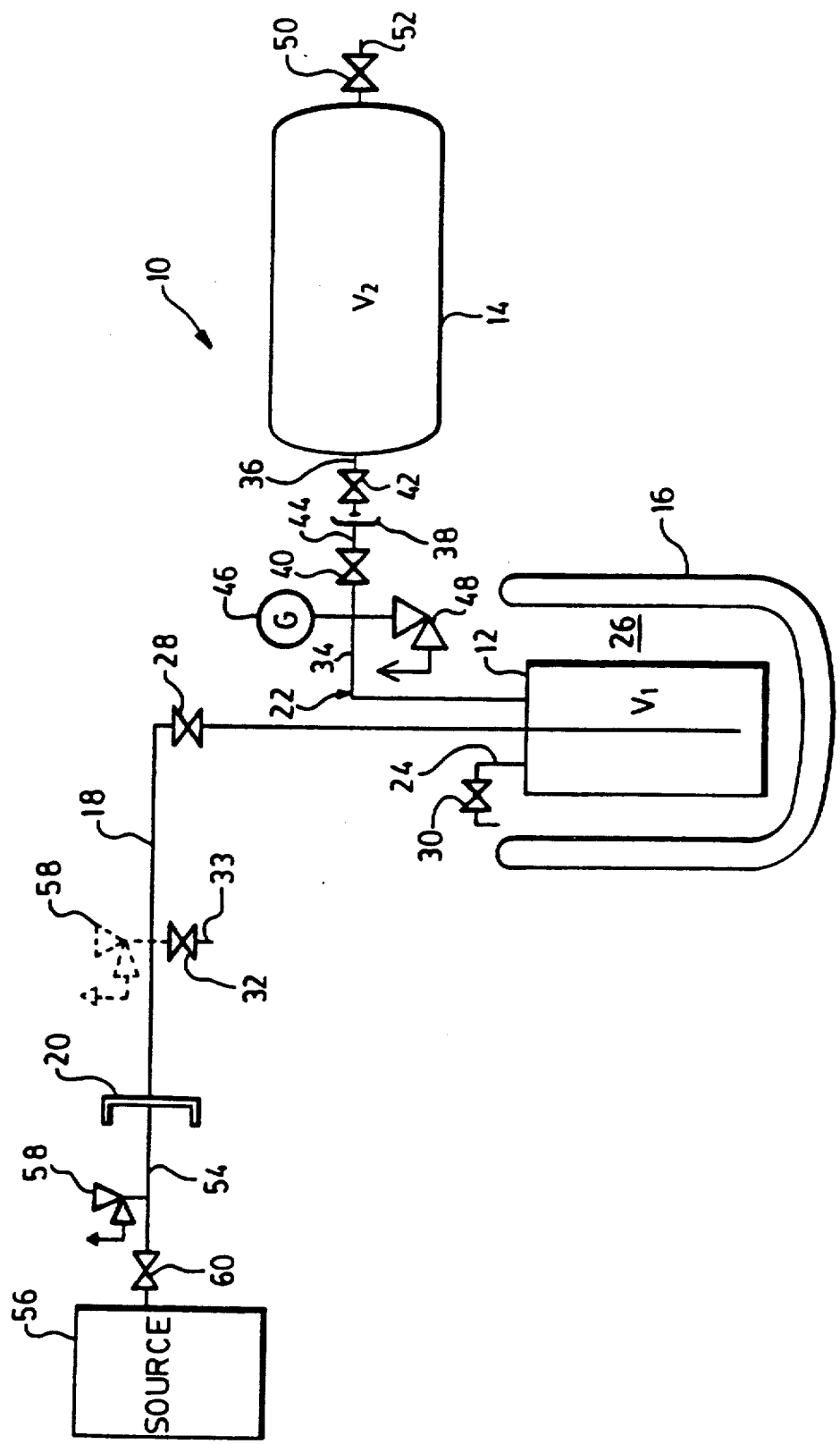

METHOD AND APPARATUS FOR SAMPLING A CRYOGENIC LIQUID FOR ANALYSIS

This invention relates to a method and apparatus for sampling a cryogenic liquid for analysis.

Cryogenic liquids, for example, liquid hydrogen, nitrogen, oxygen and argon are employed in a number of environments and have a number of industrial and commercial applications in which the user demands high purity which necessitates accurate information as to the analytical content of trace or low level amounts of contaminating gases.

Analysis is carried out on a gaseous sample of the cryogenic liquid which typically involves the use of a flash vaporizer.

A particular difficulty arises in obtaining a gas sample which has the same molar concentration of trace contaminants as the cryogenic liquid being sampled.

Thus, for example, liquid nitrogen may typically contain trace amounts of one or more of helium, hydrogen, neon, argon, oxygen, methane, carbon monoxide, carbon dioxide and water. When the temperature of the liquid nitrogen is raised, vaporization or evaporation of the nitrogen and the different contaminating gases takes place at different temperatures and thus at different points in time.

Thus any hydrogen, helium and neon tends to vaporize before the nitrogen and any argon, oxygen, methane, carbon monoxide, carbon dioxide and water tends to vaporize after the nitrogen. In this way fractionation of the sample occurs and the analytical composition of the gas sample continuously obtained varies continuously and does not accurately represent the analytical composition of the cryogenic liquid.

Apparatus has been proposed for sampling cryogenic liquids in U.S. Pat. Nos. 3,123,982, Brown et al; 3,357,256, Burch; 3,938,391, Winkler; and 3,029,627, Buban. These prior proposals have a number of disadvantages themselves to rapid repeated use for collection of a plurality of samples which is important for comparison of the analysis results.

Furthermore, these prior proposals do not fully address the problem of fractionation of the cryogenic liquid during volatilization whereby the gas sample is not a true sample of the liquid. In many cases the resulting discrepancies are not serious, however, many users are demanding liquids of ever greater purity so that it becomes increasingly necessary to be able to detect low level contaminants; This is especially so in the electronics industry.

In accordance with one aspect of the present invention, there is provided a method of sampling a cryogenic liquid which comprises: isolating a liquid sample of the cryogenic liquid in an environment at a temperature above the freezing temperature of the cryogenic liquid and not greater than the boiling temperature of the cryogenic liquid, removing the environment, allowing the isolated liquid sample to vaporize in bulk into a collection vessel, and collecting at least a bulk portion of the vaporized liquid in the collection vessel for analysis.

In an especially preferred embodiment the collection vessel and isothermal environment are part of a sampling system from which the collection vessel is readily detachable and removable for transport to a site of analysis.

In a further preferred embodiment the environment of the isolating step is one which is isothermal with the sample. This is, in particular, the case when the cryogenic liquid of the sample is also employed to establish the environment of the isolation of the sample.

The reference to an "isothermal environment" is to be understood as an environment at the same or essentially the same temperature as that of the cryogenic liquid under non-vaporizing conditions.

The reference to vaporization in "bulk" is to be understood as the intact, non-fractionated vaporization or evaporation of the cryogenic liquid to the gas state without change in molar composition such that the composition of the gas correctly reflects the composition of the liquid; and the reference to a "bulk portion" is to be understood as a quantity of the resulting gas less than the whole.

Thus in accordance with a particular embodiment the method comprises connecting a liquid sampling vessel by a flow line or conduit means to a gas collection vessel with at least a first valve in the flow line, closing the first valve to isolate the collection vessel from the sampling vessel, filling the sampling vessel with the cryogenic liquid, maintaining the wall of the sampling vessel at a first temperature at least essentially the same as the temperature of the cryogenic liquid, terminating flow of cryogenic liquid into the sampling vessel, applying a second temperature to the wall of the sampling vessel, higher than the first temperature, to vaporize the cryogenic liquid and generate gas, opening the first valve, filling the collection vessel with the generated gas, closing the first valve, and disconnecting the collection vessel with the first valve from the sampling vessel for transportation of the collection vessel.

In accordance with another aspect of the invention there is provided an apparatus for sampling a cryogenic liquid comprising a sampling vessel for housing a sample of the cryogenic liquid, first conduit means for flow of the cryogenic liquid into the sampling vessel, a gas collection vessel and a second conduit means to provide gas flow communication between the sampling vessel and the gas collection vessel.

In one especially preferred embodiment a removable chamber encompasses the sampling vessel and there is an outlet in the sampling vessel for flow of cryogenic liquid from the sampling vessel to the chamber.

In another especially preferred embodiment the gas collection vessel is detachably connected to the sampling vessel by the second conduit means.

The invention is illustrated in an especially preferred embodiment by to the accompanying drawing in which:

FIG. 1 illustrates schematically a sampling system in accordance with the invention.

With further reference to FIG. 1, a cryogenic sampling system 10 comprises a liquid sample vessel 12, a gas collection vessel 14 and an outer vessel 16.

A flow line or conduit 18 connects the interior of liquid sample vessel 12 with a connection 20 which connects the system 10 by a flexible hose 54 or the like to a source 56 of cryogenic liquid from which samples are to be taken.

A flow line or conduit 22 connects the interior of liquid sample vessel 12 with the interior of gas collection vessel 14 and an out-flow line or conduit 24 connects the interior of liquid sample vessel 12 with a space 26 defined between outer vessel 16 and the liquid sample vessel 12.

A valve 28 in flow line 18 controls flow of liquid or gas in flow line 18 and a valve 30 controls flow in out-flow line 24.

A purge valve 32 is located in a branch line 33 from the flow line 18 between connection 20 and valve 28.

A safety valve 58 in flexible hose 54 establishes a relief pressure in the event of build-up of pressure in hose 54 beyond the capacity of the hose 54. Typically this pressure may be about 300 Psig. As an alternative the safety valve 58 may be located in line 18 as shown in broken lines.

A valve 60 in hose 54 controls flow of cryogenic fluid from source 56 in hose 54.

Flow line 22 includes a line 34 communicating with the interior of vessel 12 and a line 36 communicating with the interior of vessel 14. Lines 34 and 36 are connected by a connection 38, which forms part of flow line 22.

A valve 40 controls flow in line 34 and a valve 42 controls flow in line 36, a dead volume 44 being defined between valves 40 and 42 in the region of connection 38 which is also part of line 22.

Line 34 includes a pressure gauge 46 and a safety valve 48.

A valve 50 controls flow in a line 52 communicating with the interior of vessel 14.

Liquid sample vessel 12 has a volume $V_1$ and gas collection vessel 14 has a volume $V_2$.

Generally the volume ratio $V_2:V_1$ is about 7:1.

Vessels 12 and 14 are suitably made of stainless steel, their interior surfaces being finished and treated to minimize contamination problems.

It is appropriate for flow line 18 to extend to a lower region of the interior of liquid sample vessel 12 so that liquid introduced into vessel 12 along flow line 18 fills the vessel 12 from the bottom.

It is likewise appropriate that flow line 22 and out-flow line 24 communicate with an upper region of the interior of liquid sample vessel 12.

It is a significant feature of the invention that gas collection vessel 14 is readily separated and removed from system 10 at connection 38, without altering the gas content of gas collection vessel 14. Gas collection vessel 14 is of a form readily suitable for transport for analysis of its gas content. Thus a particular advantage of the present invention is that the gas collection vessel 14 with the gas sample to be analyzed is readily removed from the system 10 for transport to an analysis site and there is no need to transport the entire system 10.

The operation of the system 10 is described below for the case of a system 10 which has previously been employed for sampling essentially the same cryogenic liquid, e.g., liquid nitrogen.

At the commencement of sampling, gas collection vessel 14 contains a gaseous sample of known analysis of the cryogenic liquid, for example, liquid nitrogen, which is to be investigated; the gaseous sample being under high pressure, typically of the order of 1500 psig derived from the previous sampling; valves 42 and 50 are closed, and line 36 is connected to line 34 by connection 38 whereby system 10 is in an assembled state.

In this initial state the vessel 12 also contains a gaseous sample of the cryogenic liquid, for example, liquid nitrogen, at high pressure, typically 1500 psig based on previous sampling. The dead volume 44 between valves 40 and 42 is maintained small and is readily purged by a controlled leak from valve 40 or 42.

With the system 10 thus assembled, the leak tightness of gas collection vessel 14 can be ascertained by opening valves 40 and 42 and observing the pressure reading on gauge 46. Thus since the volumes $V_1$ and $V_2$ are known, and the pressure of the gas collection vessel 14 is known, a simple calculation will give the leak rate of vessel 14, if there is a leak If there is a leak steps are taken to locate it and seal the leak. The rate of leak is usually an indication of the nature of the leak.

The connection 20 typically has a sealing plug (not shown) as does the flexible hose 54 to the source 56 of cryogenic liquid, and these are removed whereby connection 20 forms a connection between the source 56 of cryogenic liquid and system 10.

The flow line 18 extending between valve 28 and connection 20 and the flexible hose 54 from connection 20 to the source of cryogenic liquid can be purged by opening valves 28, 40 and 42 and employing the gas pressure in collection vessel 14 and sample vessel 12 in successive purging cycles, with intermittent closing of such valves. Valve 32 is also opened for exit of the gas under pressure. These purging cycles are continued until the gas in collection vessel 14, and also in sample vessel 12, is at atmospheric pressure. Clearly these purging cycles also serve to purge lines 18 and 22 including dead volume 44.

Valves 28, 32, 40 and 42 are closed after completion of the purging cycles.

System 10 is now in a state in which gas collection vessel 14 contains gas of known analysis at atmospheric pressure and the flow lines 18 and 22 including dead volume 44, and the flexible hose from connection 20 to the source of cryogenic-liquid have all been purged in the successive purging cycles.

Valves 30 and 50 have been maintained closed throughout the purging.

In order to take a sample of cryogenic liquid for analysis, valve 60 at the source 56 is opened whereby the cryogenic liquid starts to flow along the flexible hose 54 to connection 20 and then into flow line 18. The liquid cools down the flexible hose 54 to connection 20 and the flow line 18. This initial flow is maintained with valve 28 closed and valve 32 opened whereby liquid flows into flow line 18 and exits through branch line 33. Initially the liquid will fractionate and partially vaporize or volatilize and the flow is continued with valve 32 open until liquid flows out of branch line 33.

When cryogenic liquid flows out of branch line 33 through valve 32, valve 32 is closed and valves 28 and 30 are opened. The cryogenic liquid then flows along flow line 18 into liquid sample vessel 12, starts to collect therein and then to exit through out-flow line 24.

Initially the liquid collecting in liquid sample vessel 12 will be partially fractionated as the temperature of the liquid rises and components therein are vaporized, however, as the flow continues vessel 12 will be cooled by the flowing liquid which flows out of vessel 12 through cut-flow line 24 and into the space 26 between outer vessel 16 and sample vessel 12.

When the space 26 is filled with liquid, the cryogenic liquid which has collected in vessel 12 will have been collected at a temperature which is the same or essentially the same as its own temperature. In other words, it has been collected under isothermal conditions since the vessel 12 will have been cooled by the liquid in the space 26. Having been collected under isothermal conditions, the liquid in vessel 12 is collected without fractionation. At this stage valves 28 and 30 are closed thereby trapping a known volume of the nonfractionated cryogenic liquid sample in vessel 12. This represents a true sample of the cryogenic liquid being investigated.

The valve 60 upstream of connection 20 is then closed and valve 32 may be opened to vent the flexible hose and line 18 between valve 28 and the valve at the source of the liquid. The connection 20 and the flexible hose 54 to the source 56 are then suitably capped by reapplying the sealing plugs.

In the next stage of the operation, valves 40 and 42 are opened and outer vessel 16 is removed. With the removal of outer vessel 16, the temperature of vessel 12 begins to rise and the cryogenic liquid sample therein begins to vaporize or evaporate and passes along flow line 22 into gas collection vessel 14 developing a pressure that is measured by gauge 46.

Since the sample vessel 12 was full at the commencement of this stage, the pressure measured by gauge 46 is a function of the ratio $V_1:V_2$ and the nature of the cryogenic liquid. After an appropriate time to permit completion of the evaporation of the liquid sample in vessel 12, valves 40 and 42 are closed.

Vessel 14 now contains in gaseous form a true sample of the cryogenic liquid having, in gaseous form, the same proportionate amounts of any contaminants as the cryogenic liquid.

Vessel 14 is disconnected from system 10 at connection 38 and is ready for transport to an analysis site.

It will be recognized that at this stage liquid sample vessel 12 contains the gas under the same high pressure as in gas collection vessel 14.

The balance of system 10, without vessel 14, can then be employed to obtain a further sample of the cryogenic liquid using a fresh vessel 14 containing a sample of the gas under high pressure from a previous analysis.

In this way successive gas samples can be obtained of the cryogenic liquid utilizing a single system 10 with a plurality of vessels 14. It is advantageous to take a plurality of samples of the cryogenic liquid being investigated, the results of gas analysis can then be compared to minimize analysis errors.

This represents a significant advantage over prior art systems in which the collection vessel is an integral part of the system and the entire system is shipped for the analysis.

It will be understood that if the system 10 is to be used for sampling different cryogenic liquids, appropriate purging of the entire system with the cryogenic liquid should first be carried out. Generally, however, it is preferable to employ a particular system 10 exclusively for analysis of a particular cryogenic liquid, i.e. exclusively for liquid nitrogen or liquid oxygen.

Furthermore, when using a system 10 for the first time, or for the first time with a particular cryogenic liquid, a gas sample of the liquid is required in the vessel 14 at high pressure and this sample must be preanalyzed.

As indicated above the pressure in the vessels 12 and 14 at commencement of sampling is typically of the order of 1500 psig, this being the magnitude of pressure developed by vaporizing a volume $V_1$ of liquid to a volume $V_2$ of gas when the ratio of $V_2:V_1$ is about 7:1.

Thus vessel 12 suitably has a volume of 600 cc and vessel 14 has a volume of 3800 cc (1 U.S. gallon).

Table I below shows the gas volume in liters at 15 C. and atmospheric pressure derived from 1 liter of various common cryogenic liquids at their respective boiling point temperatures.

TABLE I

| Liquid 1 liter | Gas vol. liter |
|---|---|
| $N_2$ | 691 |
| $O_2$ | 854 |
| Ar | 835 |
| $H_2$ | 844 |
| He | 748 |

Thus generally 1 liter of cryogenic liquid produces from about 675 to 875 liters of gas.

The vessel 14 could also be under vacuum for the collection, however, this is less preferred.

In the case of an initial start up of system 10 it may be appropriate to connect a high pressure source of pure, preanalyzed gas to purge and pressurize vessels 12 and 14 and line 22; this high pressure source might conveniently be connected to valve 28. Dead volume 44 at connection 38 is purged by controlled leak through valve 40 or 42 and then by the previously described general purging.

It is also possible to connect a vaporizer to the source 56 of cryogenic liquid to provide a supply of gas to purge the vessels 12 and 14 and the lines 18 and 22 and the associated valves; the vaporizer might conveniently be connected to connection 20.

The invention provides the further advantage that the vessels 12 and 14 are readily accessible for physical and chemical treatment or cleaning.

A further advantage of the invention is that the vessel 12 is precooled externally thereby permitting use of a separate source or supply of cooling liquid, thus, for example, a bath of liquid helium can be employed instead of liquid hydrogen when sampling liquid hydrogen thereby increasing the safety of the sampling operation. Prior sampling devices do not have this flexibility. In like manner liquid nitrogen can be employed to cool liquid oxygen or liquid argon. Generally the cooling liquid should not have a boiling temperature below the freezing point of the liquid being cooled. This provides the advantage, in addition to safety, that a less expensive, more readily available cryogenic liquid, such as liquid nitrogen, can often be used for cooling more expensive cryogenic liquids such as liquid argon, especially when the latter is in short supply or only a small amount is available for sampling. In such cases a supply of, for example, liquid nitrogen in outer vessel 16 may supplement cryogenic liquid of the sample delivered through out-flow line 24.

It is also possible to speed up the vaporization of the liquid sample in vessel 12 after removal of outer vessel 16 by, for example, surrounding vessel 12 with an outer vessel of liquid such as water at ambient temperature to 100° C. This represents a further advantage of the sampling device of the invention which is not exhibited by samples of the prior art.

The pressure gauge 46 may suitably have a pressure range of 0–3000 psig with a stainless steel Bourdon tube. Safety valve 48 is conveniently set at 1800 psig, and valve 50 may suitably have a bursting disc rating of 1800 psig.

The outer vessel 16 may conveniently be a metal Dewar vessel.

The embodiments of the invention in which an exclusive property or privilege is claimed are defined as follows:

1. A method of sampling a cryogenic liquid for determination of the molar composition of the cryogenic liquid comprising:
   isolating a liquid sample of the cryogenic liquid in an environment at a sampling location which is at a temperature above the freezing temperature of the cryogenic liquid and not greater than the boiling temperature of the cryogenic liquid,
   removing said environment,
   allowing the isolated liquid sample to vaporize in bulk into a collection vessel,
   collecting the vaporized liquid in gas form in said collection vessel for analysis, and
   removing only said collection vessel from said sampling location for said analysis.

2. A method according to claim 1, wherein said collection vessel and said isolated liquid sample have a volume ratio of about 7:1.

3. A method according to claim 1 or 2, wherein said environment is isothermal with said liquid sample.

4. A sampling method for a cryogenic liquid comprising the steps of:
   connecting a liquid sampling vessel to a gas collection vessel with at least a first valve in the connection,
   closing said first valve to isolate said collection vessel from said sampling vessel,
   filling said sampling vessel with said cryogenic liquid,
   maintaining a wall of said sampling vessel at a first temperature which is at least about the temperature of said cryogenic liquid,
   cutting off the flow of said cryogenic liquid into said sampling vessel,
   applying a second temperature, higher than said first temperature, around said wall of said sampling vessel in order to vaporize said cryogenic liquid and to generate gas,
   opening said first valve,
   filling said collection vessel with said generated gas,
   closing said first valve, and
   disconnecting said collection vessel and said first valve from said sampling vessel for transportation of said collection vessel.

5. A sampling method according to claim 4, further including the steps of:
   measuring the pressure of said generated gas during the filling of said collection vessel and closing said first valve as soon as the measured pressure is about constant.

6. A sampling method according to claim 4, wherein said collection vessel is purged before being filled by gas generated from the cryogenic liquid.

7. A method according to claim 4, wherein said collection vessel is purged with gas generated from the cryogenic liquid before closing said first valve to isolate said collection vessel from said sampling vessel.

8. A method according to claim 6 or 7, wherein said collection vessel comprises a second valve for venting gas inside said collection vessel.

9. An apparatus for sampling a cryogenic liquid for determination of the molar composition of the cryogenic liquid, comprising:
   a sampling vessel for housing a sample of the cryogenic liquid,
   first conduit means for flow of the cryogenic liquid into said sampling vessel,
   a removable chamber encompassing said sampling vessel,
   an outlet in said sampling vessel for flow of cryogenic liquid from said sampling vessel to said chamber,
   a gas collection vessel,
   second conduit means adapted to provide gas flow communication between said sampling vessel and said gas collection vessel, wherein said gas collection vessel is detachably connected to said sampling vessel by said second conduit means.

10. An apparatus according to claim 9, wherein said gas collection vessel and said sampling vessel have a volume ratio of about 7:1.

* * * * *